US012630513B2

(12) United States Patent
Pottabathini et al.

(10) Patent No.: US 12,630,513 B2
(45) Date of Patent: May 19, 2026

(54) PROCESS FOR THE PREPARATION OF TRIGONELLINE OR PHARMACEUTICALLY ACCEPTABLE SALTS THEREOF

(71) Applicant: LAURUS LABS LIMITED, Hyderabad (IN)

(72) Inventors: Narender Pottabathini, Hyderabad (IN); Aravinda Kumar Madugula, Hyderabad (IN); Ashok Sakhamuri, Hyderabad (IN); Ravindra Appani, Hyderabad (IN)

(73) Assignee: Laurus Labs Limited, Hyderabad (IN)

( * ) Notice: Subject to any disclaimer, the term of this patent is extended or adjusted under 35 U.S.C. 154(b) by 943 days.

(21) Appl. No.: 17/780,584

(22) PCT Filed: Nov. 2, 2021

(86) PCT No.: PCT/IB2021/060119

§ 371 (c)(1),
(2) Date: May 27, 2022

(87) PCT Pub. No.: WO2022/097017

PCT Pub. Date: May 12, 2022

(65) Prior Publication Data

US 2023/0348391 A1 Nov. 2, 2023

(30) Foreign Application Priority Data

Nov. 5, 2020 (IN) ............................ 202041048428

(51) Int. Cl.
*C07D 213/803* (2006.01)
*C07D 213/80* (2006.01)

(52) U.S. Cl.
CPC ....... *C07D 213/803* (2013.01); *C07D 213/80* (2013.01)

(58) Field of Classification Search
CPC .......................... C07D 213/803; C07D 213/80
See application file for complete search history.

(56) References Cited

FOREIGN PATENT DOCUMENTS

| | | | | |
|---|---|---|---|---|
| CN | 101089166 | A | | 12/2007 |
| CN | 101967121 | A | | 2/2011 |
| CN | 102304085 | A | | 1/2012 |
| CN | 102304085 | | * | 1/2014 |
| CN | 103755630 | A | | 4/2014 |
| CN | 106496111 | A | | 3/2017 |
| EP | 0984005 | A1 | | 3/2000 |

OTHER PUBLICATIONS

Donoso, Int J Neuro, 2019, vol. 22(12), 765-777. (Year: 2019).*
Ashihara, Nat Prod Comm, 2016, vol. 11(8), 1093-1096. (Year: 2016).*
Kalaska, J Agric Food Chem, 2014, 62, 2853-2860. (Year: 2014).*
Lang, J Agric Food Chem, 2008, 56, 11114-11121. (Year: 2008).*
Sarett, H.P., Perlzweig, W.A., & Levy, E.D. (1940). Synthesis and excretion of trigonelline. Journal of Biological Chemistry, 135 (2); pp. 483-485.
J. Am. Chem. Soc. 1941, 63, 8, 2283-2284.

* cited by examiner

*Primary Examiner* — D Margaret M Seaman
(74) *Attorney, Agent, or Firm* — Blank Rome LLP

(57) ABSTRACT

The present invention generally relates to an improved process for the preparation of Trigonelline or pharmaceutically acceptable salts thereof and to processes for its purification.

18 Claims, No Drawings

PROCESS FOR THE PREPARATION OF TRIGONELLINE OR PHARMACEUTICALLY ACCEPTABLE SALTS THEREOF

CROSS-REFERENCE TO RELATED APPLICATIONS

This is a national phase application that is based on and claims the benefit of International Application No. PCT/IB2021/060119, filed on Nov. 2, 2021, which is based on and claims the benefit under Indian Provisional Application No. 202041048428 filed on Nov. 5, 2021, and entitled "An improved process for the preparation of trigonelline or pharmaceutically acceptable salts thereof," the contents of each of which are incorporated by reference herein.

FIELD OF THE INVENTION

The present invention relates to an improved process for the preparation of Trigonelline or pharmaceutically acceptable salts thereof and to processes for its purification.

BACKGROUND OF THE INVENTION

Trigonelline (N-methylnicotinate) is a pyridine alkaloid and is a zwitterion formed by the methylation of the nitrogen atom of niacin (vitamin B3). It has the following chemical structure:

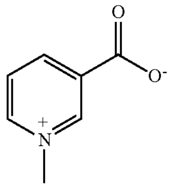

Trigonelline

Trigonelline is a product of niacin metabolism and also occurs in many plants and animals. It has been isolated from fenugreek seeds (*Trigonella foenum-graecum*), garden peas, hemp seed, oats, potatoes, *Stachys* species, dahlia, *Strophanthus* species and *Dichapetalum cymosum*. Trigonelline has a GRAS (Generally Recognized as Safe) status by the FDA. Numerous biological activities have been reported for Trigonelline such as protection of heart and liver and treatment of hyperglycemia, hypercholesterolemia, nervous and hormonal disorders, and cancers apart from nutritional benefits.

Trigonelline is mainly extracted from the fenugreek, but its content is low accounting to only 0.1037-0.3548%. This process requires a large amount of organic solvents and the extraction and refining process is quite tedious, time-consuming and eventually cost is high.

Journal of Biological Chemistry 1940, Vol. 135, pp. 483-485 disclosed preparation of Trigonelline by treating nicotinic acid with dimethyl sulfate at 130° C. The resulting viscous mass was dissolved in water and treated with sulfuric acid followed by evaporation of the reaction mass resulting thick syrup which was poured into hot alcohol, decolorized and crystallized to obtain pure trigonelline acid sulfate. Concentration of the mother liquor and addition of alcohol gave a further crop of pure crystals. The yield was 65% of the calculated amount.

The Chinese patent application No. 102304085 disclosed process for synthesizing trigonelline hydrochloride from nicotinic acid and dimethyl carbonate in the presence of potassium carbonate followed by treatment with hydrochloric acid and recrystallization from 70% ethanol.

Furthermore, several techniques are known in the art for the extraction of trigonelline from plant sources, for e.g., by employing ultrasonic treatment followed by alumina column as disclosed in CN101967121 and CN106496111; or by using ultrahigh-pressure extraction mode as disclosed in CN103755630 or by enzymolysis process as disclosed in CN101089166. All these processes are cumbersome, uneconomical, requires high amounts of extraction solvents and not suitable on commercial scale. Processes involving extraction from plant materials require specialized techniques or excess solvents which is not economical on large scale.

The processes disclosed under the above literatures have certain drawbacks as it involves mainly solvent free reaction in the methylation step at higher temperatures and this step leads to formation of methyl ester impurities thereby getting the end product with lower yield and less pure. In view of this, it would be desirable to produce Trigonelline or pharmaceutically acceptable salts thereof in high yield that enables the effective control of the formation of trigonelline methyl ester impurity in reproducible manner.

Hence, the present invention relates to a process for the preparation of Trigonelline or pharmaceutically acceptable salts thereof which overcomes drawbacks associated with the prior art processes. The current process is not only advantageous in producing Trigonelline or pharmaceutically acceptable salts thereof in high yields but also reduces the formation of by-products and use of less quantity of costly and hazardous dimethyl sulphate thereby reducing the cost of production which is very practical at large scale production.

Further, the present invention also provides ways to purify Trigonelline or pharmaceutically acceptable salts thereof.

SUMMARY OF THE INVENTION

Accordingly, the present invention provides an improved process for the preparation of Trigonelline or pharmaceutically acceptable salts thereof in high yields.

In accordance with another embodiment, the present invention provides an improved process for the preparation of Trigonelline or pharmaceutically acceptable salts thereof of formula I,

I

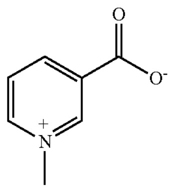

comprising:

a) reacting nicotinic acid of formula II with dimethyl sulfate in a suitable organic solvent to obtain a compound of formula III, and

II

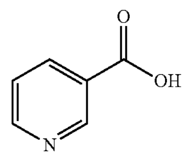

III

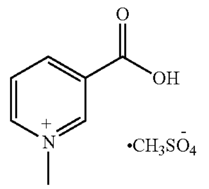

b) converting the compound of formula III in to trigonelline or pharmaceutically acceptable salts thereof of formula I.

In accordance with another embodiment, the present invention provides an improved process for the preparation of Trigonelline or pharmaceutically acceptable salts thereof of formula I, comprising:

a) reacting nicotinic acid of formula II with dimethyl sulfate in a suitable organic solvent selected from the group consisting of alcohols, ketones, ethers, esters, halogenated solvents, cyclic hydrocarbons, aromatic hydrocarbons, nitriles, amides and the like and mixtures thereof to obtain a compound of formula III; and b) converting the compound of formula III in to trigonelline or pharmaceutically acceptable salts thereof of formula I.

In accordance with another embodiment, the present invention provides an improved process for the preparation of Trigonelline or pharmaceutically acceptable salts thereof of formula I,

I

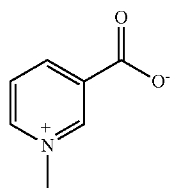

comprising:

a) reacting nicotinic acid of formula II with dimethyl sulfate in a suitable organic solvent to obtain a compound of formula III,

II

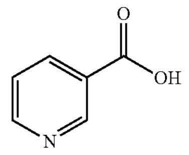

-continued

III

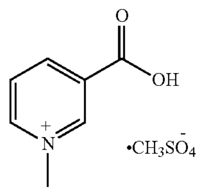

b) reacting the compound of formula III with an acid to obtain salt of compound of formula IV; and

IV

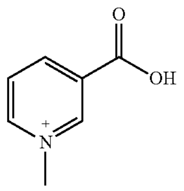

c) converting the salt of compound of formula IV in to trigonelline or pharmaceutically acceptable salts thereof of formula I.

In accordance with another embodiment, the present invention provides an improved process for the preparation of Trigonelline or pharmaceutically acceptable salts thereof of formula I, comprising:

a) reacting nicotinic acid of formula II with dimethyl sulfate in a suitable organic solvent to obtain a compound of formula III;

b) reacting the compound of formula III with an acid to obtain salt of compound of formula IV; and c) converting the salt of compound of formula IV in to trigonelline or pharmaceutically acceptable salts thereof of formula I; wherein the suitable organic solvent is selected from the group consisting of alcohols, ketones, ethers, esters, halogenated solvents, cyclic hydrocarbons, aromatic hydrocarbons, nitriles, amides, and the like and mixtures thereof.

In accordance with another embodiment, the present invention provides an improved process for the preparation of Trigonelline or pharmaceutically acceptable salts thereof of formula I, comprising:

a) reacting nicotinic acid of formula II with dimethyl sulfate in a ketone solvent to obtain a compound of formula III, b) reacting the compound of formula III with sulfuric acid, c) isolating the Trigonelline sulfate of compound of formula IV, d) neutralizing the compound of formula IV with a base to obtain Trigonelline.

In another embodiment, the present invention provides a process for purification of Trigonelline or pharmaceutically acceptable salts thereof of formula I.

In another embodiment, the present invention provides a process for purification of Trigonelline or pharmaceutically acceptable salts thereof of formula I, comprising:

a) treating Trigonelline or pharmaceutically acceptable salts thereof of formula I with a suitable solvent; and b) isolating pure Trigonelline or pharmaceutically acceptable salts thereof of formula I; wherein the suitable solvent is selected from alcohols; ethers; nitriles; aromatic hydrocarbons; aliphatic hydrocarbons; halogenated hydrocarbons; ketones; esters; water, or mixtures thereof.

In accordance with another embodiment, the present invention provides an improved process for the preparation of Trigonelline or pharmaceutically acceptable salts thereof of formula I, comprising:

a) reacting nicotinic acid of formula II with dimethyl sulfate in a ketone solvent at a temperature of about room temperature to about reflux to obtain compound of formula III,
b) reacting the compound of formula III with sulfuric acid at about room temperature to about reflux,
c) isolating the Trigonelline sulfate of compound of formula IV,
d) neutralizing the compound of formula IV with a base to obtain Trigonelline,
e) purifying the trigonelline with a suitable solvent; and
f) isolating the pure Trigonelline.

In another embodiment, the present invention provides a pharmaceutical composition comprising trigonelline or pharmaceutically acceptable salts thereof obtained by the process of the present invention and at least one pharmaceutically acceptable excipient.

DETAILED DESCRIPTION OF THE INVENTION

The present invention provides an improved process for the preparation of Trigonelline or pharmaceutically acceptable salts thereof.

In accordance with another embodiment, the present invention provides an improved process for the preparation of Trigonelline or pharmaceutically acceptable salts thereof of formula I,

I

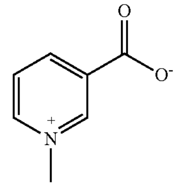

comprising:

a) reacting nicotinic acid of formula II with dimethyl sulfate in a suitable organic solvent to obtain a compound of formula III, and

II

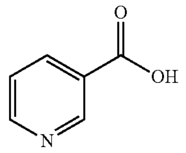

III

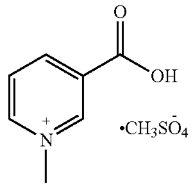

b) converting the compound of formula III in to trigonelline or pharmaceutically acceptable salts thereof of formula I.

In accordance with another embodiment, the present invention provides an improved process for the preparation of Trigonelline or pharmaceutically acceptable salts thereof of formula I,

I

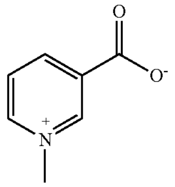

comprising:

a) reacting nicotinic acid of formula II with dimethyl sulfate in a suitable organic solvent to obtain compound of formula III;

II

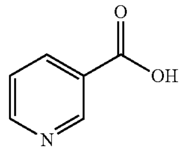

III

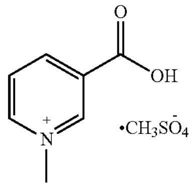

b) reacting the compound of formula III with an acid to obtain salt of compound of formula IV; and

IV

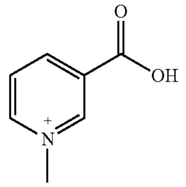

c) converting the salt of compound of formula IV in to trigonelline or pharmaceutically acceptable salts thereof of formula I.

In a preferred embodiment, the present invention provides an improved process for the preparation of Trigonelline or pharmaceutically acceptable salts thereof of formula I, comprising:

a) reacting nicotinic acid of formula II with dimethyl sulfate in a suitable organic solvent to obtain compound of formula III;
b) reacting the compound of formula III with sulfuric acid to obtain salt of compound of formula IV; and
c) converting the salt of compound of formula IV in to trigonelline or pharmaceutically acceptable salts thereof of formula I; wherein the suitable organic solvent is selected from the group consisting of alcohols, ketones, ethers, esters, halogenated solvents, cyclic hydrocarbons, aromatic hydrocarbons, nitriles, amides and the like and mixtures thereof.

In accordance with another embodiment, the present invention provides an improved process for the preparation of Trigonelline or pharmaceutically acceptable salts thereof of formula I, comprising:

a) reacting nicotinic acid of formula II with dimethyl sulfate in a ketone solvent to obtain compound of formula III,
b) reacting the compound of formula III with sulfuric acid,
c) isolating the Trigonelline sulfate of compound of formula IV,
d) neutralizing the compound of formula IV with a base to obtain Trigonelline.

Nicotinic acid of formula II is commercially available or can be prepared, for e.g. according to EP 0984005 or J. Am. Chem. Soc. 1941, 63, 8, 2283-2284.

According to prior art processes to prepare trigonelline there are several disadvantages associated with the processes, as it involves use of dimethyl sulfate in excess which not only makes the cost of the product relatively high, but also the final product gets contaminated with dimethyl sulfate, which is known to be genotoxic. Further, requires high reaction temperatures which are not advisable on large scale as it may have adverse effect on the product. Moreover, due to use of excess dimethyl sulfate and the reaction at higher temperatures resulted trigonelline gets contaminated with by-product trigonelline methyl ester, which ultimately leading to yield loss.

To overcome the difficulties associated with the known processes, the present inventors have tried to improve the process conditions for preparing Trigonelline or pharmaceutically acceptable salts thereof, but encountered several problems such as:

i) when higher amounts of dimethyl sulfate is used, the reaction mass was very thick which severely reduced the pace of stirring;
ii) employing high reaction temperatures produced the product in less time but at the same time the by-product trigonelline methyl ester was produced in a range of 20 to 30%;
iii) Yield of the product was low due to the formation of the by-product trigonelline methyl ester.

The present invention specifically provides an improved process to prepare Trigonelline or pharmaceutically acceptable salts thereof with high yield and high purity when compared to known processes and that overcomes the aforementioned drawbacks.

Step a) of the forgoing process may include reacting nicotinic acid of formula II with dimethyl sulfate in a suitable organic solvent to obtain compound of formula III.

Dimethyl sulfate may be added from about 0.5 to about 1.4 mole equivalents per mole of starting nicotinic acid, preferably about 0.8 to about 1.2 moles; more preferably about 1:1 moles.

Examples of suitable organic solvent include but are not limited to alcohols such as methanol, ethanol, isopropanol, n-butanol, and the like; ketones such as acetone, methyl isobutyl ketone and the like; ethers such as tetrahydrofuran, diethyl ether, 1,4-dioxane, methyl tert. butyl ether, cyclopentyl methyl ether and the like; esters such as methyl acetate, ethyl acetate, isopropyl acetate, n-propyl acetate, n-butyl acetate, t-butyl acetate and the like; halogenated solvents such as methylene chloride, chloroform, carbon tetrachloride and the like; cyclic hydrocarbon solvents such as cyclohexane and the like; aromatic hydrocarbon solvents such as toluene and the like; nitriles such as acetonitrile, propionitrile, benzonitrile and the like; amides such as dimethylformamide, dimethyl acetamide and mixtures thereof. Preferably the organic solvent is selected from the group consisting of methanol, isopropanol, ethyl acetate, methyl isobutyl ketone, acetone, acetonitrile; more preferably the organic solvent is acetone.

The reaction may typically be carried out at a suitable temperature such as room temperature to reflux temperature of the solvent. Preferably, the reaction temperature is about 50° C. to about 100° C. The reaction is allowed to stir for a period of time from about 2 hrs to until completion of the reaction, preferably 4-15 hrs.

The resulting reaction mass containing compound of Formula III is continued directly to the next step without isolating the said intermediate or alternatively isolated by conventional techniques such as cooling to 10° C. to about 50° C. and filtration.

It has been observed that preparation of compound III according to known processes always resulted in formation of trigonelline methyl ester of formula Ma as an impurity in the range of 20 to 30% which is generated due to the presence of excess of dimethyl sulfate (1.5 mole equivalents) and at high temperature conditions (130-135° C.). Though this impurity is removed during the post processing steps the yield of the final product, trigonelline, is always compromised due to loss of about 20-30% valuable material as an impurity in the form of compound of formula Ma. The present inventors have found that use of excess dimethyl sulfate together with higher temperatures resulted in spontaneous reaction which proceeds fast to form compound III along with higher amounts of compound Ma which makes the process commercially unviable.

IIIa

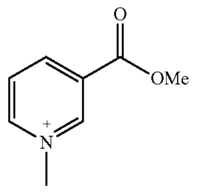

The present inventors have surprisingly found that the formation of the impurity Ma can be significantly minimized by reducing the quantity of the reactant used, i.e. dimethyl sulfate and by lowering the temperature of the reaction; thereby producing trigonelline in good yields and devoid of residual dimethyl sulfate, which is a known genotoxic compound. This process proceeds sufficiently slowly with reduced dimethyl sulfate and at lower reaction temperatures thereby minimizing the formation of impurity Ma.

Therefore, the present invention provides compound of formula III having less than 5% of compound Ma as measured by HPLC; preferably less than 4% by HPLC with the aforementioned reaction conditions of the present invention.

Further, use of excess dimethyl sulfate according to known processes led to the formation of very thick reaction mass within no time and mixing of reagents becomes practically impossible, requiring the use of specialized equipment to stir the thick reaction mass. Due to the reduction in pace of stirring, the reagents are not properly mixed leading to improper heating of the reaction mass and temperature shooting up and formation of the impurities.

In contrast, the process of the present invention reduces the amount of dimethyl sulfate used and uses solvent in the reaction which leads to proper mixing of the reaction mass and providing effective control in the reaction temperatures. Further, due to the effective stirring of the reaction mass and control of the temperature, the formation of impurities is greatly minimized leading to higher yields which are very economical on largescale.

Step b) of the forgoing process may include adding water to the compound of formula III obtained in step a) and reacting with an acid to obtain salt of compound of formula IV.

Suitable acids for use in the step b) process includes but not limited to hydrochloric acid, hydrobromic acid, hydrofluoric acid, hydroiodic acid, sulfuric acid, phosphoric acid, nitric acid, perchloric acid, boric acid, and the like. Preferably, the acid is selected from sulfuric acid or hydrochloric acid.

The step b) reaction is typically carried out at a suitable temperature such as about 40° C. to about reflux temperature. Preferably, the reaction temperature is about 40° C. to about 100° C. and is allowed to stir for a period of time from about 30 mins until completion of the reaction, preferably 1-8 hrs.

After completion of the reaction, the resultant reaction mass may be concentrated under vacuum and optionally co-distilled with suitable organic solvents, which are not limited to methanol, ethanol, isopropanol, n-butanol, acetone and the like, to obtain salt of compound of formula IV. This compound can be used as such in the subsequent reaction or can be isolated by treating with a suitable solvent. The suitable solvent utilized for isolating the salt of compound of formula IV is selected from ethanol, isopropanol, n-butanol, dichloromethane, toluene, acetone, diisopropyl ether, ethyl acetate, dimethyl formamide and the like or mixture thereof, preferably isopropanol.

Typically, the compound of formula IV is mixed with a suitable solvent as stated herein before and stirred at a temperature of about 30° C. to reflux, preferably about 50° C. to about 80° C., for a period of 20 mins to 3 hrs. The resultant reaction mass is allowed to cool to a temperature of about 20° C. to about 40° C. and stirred for a period of time from about 30 mins to about 3 hrs. Isolation of the product may be done according to conventional techniques, for example filtration and drying using any of the known methods.

Step c) of the foregoing process involves conversion of the salt of compound of formula IV in to trigonelline of formula I. Preferably, the conversion is carried out by neutralizing the salt of compound of formula IV with a suitable base at a pH of the reaction mass to about 5.5 to about 8.5. The step c) reaction may be carried out in a solvent medium, preferably with an alcohol or aqueous base more preferably using water as solvent.

Suitable base includes but are not limited to inorganic base such as alkali metal hydroxides such as lithium hydroxide, sodium hydroxide, potassium hydroxide and the like; alkali metal hydrides such as lithium hydride, sodium hydride and the like; alkali metal alkoxides such as sodium methoxide, sodium ethoxide, sodium tert-butoxide, potassium tert-butoxide and the like; alkali metal carbonates such as lithium carbonate, sodium carbonate, potassium carbonate and the like; alkali metal bicarbonates such as sodium bicarbonate and potassium bicarbonate and the like; organic bases such as triethylamine, isopropyl ethylamine, diisopropyl amine, diisopropyl ethylamine, N-methyl morpholine, piperidine, pyridine; or mixtures thereof, preferably the base is sodium methoxide, sodium carbonate, potassium carbonate, sodium hydroxide, sodium bicarbonate, potassium bicarbonate; more preferably sodium hydroxide.

The resulting reaction mass may be distilled under vacuum and optionally co-distilled with organic solvents such as methanol, ethanol, isopropanol and the like, followed by adding suitable organic solvent and isolating the trigonelline.

Typically, trigonelline thus formed may contain substantial amounts of by-products such as salt by-products which may contaminate the product and needs to be removed.

Hence, it is an object of the present invention to provide a process for the preparation of trigonelline substantially free of salt by-products comprising treating trigonelline with a suitable organic solvent selected from methanol, ethanol, isopropanol, n-butanol and the like, preferably methanol.

Typically the process is carried out by treating trigonelline containing salt by products such as sodium sulfate or sodium hydroxide, with an organic solvent at a temperature of about 10° C. to about 50° C. and stirring for a period of time from about 10 mins to about 2 hrs to completely precipitate and remove the salt by-products by conventional techniques, for example by filtration and the resultant trigonelline may be isolated from the filtrate by any of the conventional processes. For e.g., filtrate is concentrated under vacuum followed by co-distilling with organic solvents such as ethanol, isopropanol, n-butanol, acetone, toluene, ethyl acetate and the like, preferably isopropanol.

Further it has been observed that trigonelline is always prone to contaminate with substantial amounts of starting material, nicotinic acid of formula II with greater than 0.5% and inorganic salt by-products thereby the final product fails to meet regulatory requirements on purity of the final product and test of residue on ignition. In order to meet regulatory standards the contaminants needs to be removed by purification. While the present inventors tried to establish a purification process, the process is effective in the removal of the nicotinic acid of formula II from trigonelline, but failed to achieve the object as the purification of trigonelline either resulted in product loss due to high solubility of the product in the chosen solvent and/or failed to limit the residual solvent limit and residue on ignition test.

Hence, it is further object of the present invention to provide process for the preparation of trigonelline or pharmaceutically acceptable salts thereof, by minimizing the presence of any contaminants, salt by-products or residual solvents during the reactions, which is simple, easy to operate during scale-up and eco-friendly.

This problem has been addressed by the present invention by providing a process for the preparation of substantially pure trigonelline comprising purification of trigonelline from suitable solvent.

In another embodiment, the present invention provides a process for purification of Trigonelline or pharmaceutically acceptable salts thereof of formula I, comprising:

a) treating Trigonelline or pharmaceutically acceptable salts thereof of formula I with a suitable solvent; and
b) isolating pure Trigonelline or pharmaceutically acceptable salts thereof of formula I.

In a preferred embodiment, the present invention provides a process for purification of Trigonelline or pharmaceutically acceptable salts thereof of formula I, comprising:

a) dissolving or suspending Trigonelline or pharmaceutically acceptable salts thereof of formula I in a suitable solvent at about 40° C. to reflux temperature,
b) cooling the step a) solution to less than 40° C., and
c) isolating the pure Trigonelline or pharmaceutically acceptable salts thereof.

Typically, the step a) may be carried out by heating the reaction mass to a temperature of about 40° C. to reflux temperature, preferably to a temperature of about 60° C. to about 80° C.; and then cooling the solution to less than 40° C., preferably less than room temperature to precipitate out the product.

The suitable solvent useful in the purification of trigonelline comprises of alcohols such as ethanol, isopropanol, butanol and the like; ethers such as tetrahydrofuran, methyl tertiary butyl ether, diisopropyl ether, diethyl ether and the like; nitriles such as acetonitrile, propionitrile and the like; aromatic hydrocarbons such as toluene, xylene and the like; aliphatic hydrocarbons such as heptane, hexane, cyclohexane, methyl cyclohexane and the like; halogenated hydrocarbons such as dichloromethane, dichloroethane, chloroform and the like; ketones such as acetone, methyl ethyl ketone, methyl isobutyl ketone and the like; esters such as ethyl acetate, methyl acetate, isopropyl acetate and the like; water, or mixtures thereof, preferably the suitable organic solvent is selected from ethanol, acetone, ethyl acetate, isopropanol or water; more preferably isopropanol, water or its mixtures thereof.

Isolation of trigonelline may be carried out by employing conventional techniques, for example filtration, and the resultant wet product may be dried at a temperature of about 20° C. to about 70° C. for a period of about 1 hour to 15 hours. Drying can be suitably carried out in a vacuum tray dryer, vacuum oven, air oven, Rotocone Vacuum Dryer, Vacuum Paddle Dryer fluidized bed drier, spin flash dryer, flash dryer and the like.

In one embodiment, the purification of Trigonelline is carried out using isopropanol.

In another embodiment, the purification of Trigonelline is carried out using mixture of isopropanol and water.

According to the present invention, high purity Trigonelline or pharmaceutically acceptable salts thereof of formula I is obtained having a chemical purity of at least about 98%, as measured by HPLC, preferably at least about 99%, as measured by HPLC, and more preferably at least about 99.8%, as measured by HPLC; substantially free of nicotinic acid of formula II.

As used herein, the term “substantially free” refers to Trigonelline or pharmaceutically acceptable salts thereof of formula I having less than 0.1% as measured by HPLC of nicotinic acid of formula II; preferably less than 0.05% of nicotinic acid of formula II as measured by HPLC.

In another embodiment, the present invention provides Trigonelline or pharmaceutically acceptable salts thereof of formula I having less than 0.1% as measured by HPLC of nicotinic acid of formula II.

Trigonelline or pharmaceutically acceptable salts thereof of formula I obtained as above almost removes any inorganic salt completely and the residue on ignition (ROI) is less than 0.3%. Thus, the purification process of the present invention is also effective in removing any inorganic salts and the trigonelline thus obtained having residue on ignition content meeting the pharmacopoeial requirements.

In another embodiment, the present invention provides Trigonelline or pharmaceutically acceptable salts thereof of formula I having a residue on ignition less than about 0.3 percent by weight, obtained by the process of the present invention.

In another embodiment, the present invention provides Trigonelline or pharmaceutically acceptable salts thereof of formula I having a residue on ignition less than about 0.3 percent by weight.

In another embodiment, the present invention provides a pharmaceutical composition comprising trigonelline or pharmaceutically acceptable salts thereof obtained by the process of the present invention and at least one pharmaceutically acceptable excipient.

EXAMPLES

The following non-limiting examples illustrate specific embodiments of the present invention. They are not intended to be limiting the scope of the present invention in any way.

Comparative Example

Nicotinic acid (50 gms, 0.40 moles) and dimethyl sulfate (77 gms, 0.61 moles) were added into round bottom flask and stirred the contents for 10 min at 25-35° C. The reaction mass was slowly heated to reflux (127-133° C.) and maintained for 4 hrs for reaction completion (compound Ma impurity content: 20-30%). The reaction mass was allowed to cool to 25-35° C., added DM water (400 ml) and stirred for 10 min. Sulfuric acid (2 ml) was slowly added into reaction mass at 25-35° C. and concentrated the reaction mass completely below 70° C. under vacuum. Isopropanol (50 ml) was added to the reaction mass and co-distilled under reduced pressure below 70° C. Isopropanol (350 ml) was added to the reaction mass at 55-65° C. and stirred for 10 min. The reaction mass was allowed to Cool to −5° C. to 5° C. and stirred for 2 hrs. Filtered the solids, washed with isopropanol (50 ml) and suck dried the wet solid for 30 min.

DM water (150 ml) was added to the wet solid and stirred for 15 min and cooled the contents to −5° C. to 5° C., pH adjusted to 7.0-7.5 with 10% w/v sodium hydroxide solution and stirred for 15 min. The reaction mass was distilled at 70° C. under vacuum followed by co-distilling with methanol (50 ml). Methanol (400 ml) was added, heated to 60-65° C. and stirred for 30 min. The reaction mass was allowed to cool to 25-35° C., filtered the salts and washed with methanol (50 ml). Distilled the filtrate at 60° C. under vacuum, added isopropanol (250 ml), heated to 60-65° C. and stirred for 15 min. Cooled the reaction mass to −5° C. to 5° C., stirred for 2 hrs, filtered the solids and washed with cold isopropanol (50 ml). The wet solid was dried in vacuum oven at 40-45° C. for 6-8 hrs to get 25 gms of trigonelline. HPLC Purity: 99.5%.

Example 1

Nicotinic acid (100 gms, 0.81 moles) and dimethyl sulfate (108 gms, 0.85 moles) were added to acetone (1.5 Lts) in a round bottom flask at 25-35° C. The reaction mass was heated to reflux (55-65° C.) and maintained for 9-12 hrs for reaction completion (compound Ma impurity content: <4%). The reaction mass was allowed to cool to 25-35° C., and stirred at the same temperature for 40-60 mins. The resulting solids were filtered and suck dried to get compound of formula III.

DM water (500 ml) and sulfuric acid (20 ml) were added to compound of formula III obtained above. The reaction mass was heated to 85-95° C. and stirred for 6-8 hrs at the same temperature. The reaction mass was allowed to cool to 60° C. and distilled out water completely under vacuum at below 70° C. Isopropanol (100 ml) was added to the reaction mass at 45-55° C., co-distilled under reduced pressure below 70° C., degassed. Isopropanol (700 ml) was added to the reaction mass, heated to 65-75° C. and stirred for 60-90 mins. The reaction mass was allowed to cool to 25-35° C. and stirred for 60-90 mins. Filtered the solids, washed with isopropanol (100 ml) and suck dried the wet solid.

DM water (300 ml) was added to the wet solid and stirred for 10-15 min at 25-35° C. The reaction mass pH was adjusted to 6.0-6.5 with 10% sodium hydroxide solution. The reaction mass was distilled at below 70° C. under vacuum followed by co-distilled with isopropanol (100 ml) under reduced pressure below 70° C. Methanol (100 ml) was added to the reaction mass and was distilled at below 60° C. under vacuum and degassed for 1 hr. Methanol (500 ml) was added at 35-45° C., allowed to cooled to 15-25° C. and stirred for 30 mins at 15-25° C. Filtered the solids, washed with methanol (50 ml) and distilled the filtrate below 60° C. under vacuum. The reaction mass was cooled to 45-55° C., added isopropanol (100 ml) and co-distilled at below 60° C. under vacuum. Added isopropanol (700 ml) at 35-45° C., heated to 65-75° C. and stirred for 60-90 mins. Cooled the mass to 25-35° C., stirred for 60-90 mins, filtered the solids and washed with isopropanol (100 ml). Dry the wet solid in vacuum oven at 25-35° C. for 1-2 hrs and at 50-60° C. for 8-12 hrs to get 94.4 gms of trigonelline.

HPLC Purity: 99.5%; content of nicotinic acid of formula II: 0.01%.

Residual solvents: Methanol: 211 ppm; Isopropanol: 498 ppm.

Example 2

Trigonelline (15 gms; having purity: 98.68% and content of nicotinic acid of formula II: 1.1%) in isopropanol (105 ml) was heated to 65-75° C. and stirred for 60-90 mins at the same temperature. Cooled the mass to 25-35° C. and stirred at the same temperature for 60-90 mins. The resulting solids were filtered, washed with isopropanol (100 ml) and suck dried. The wet solid was further dried in vacuum oven at 25-35° C. for 1-2 hrs and at 50-60° C. for 8-12 hrs to get 11.5 gms of trigonelline.

HPLC Purity: 99.7%; content of nicotinic acid of formula II: 0.01%.

Residual solvents: Methanol: 277 ppm; Isopropanol: 609 ppm.

Example 3

Trigonelline (15 gms; ROI: 0.45% w/w) in a mixture of 5% water in isopropanol (700 ml) was heated to 65-75° C. and stirred for 60-90 mins at the same temperature. Cooled the mass to 25-35° C. and stirred at the same temperature for 60-90 mins. The resulting solids were filtered, washed with isopropanol (100 ml) and suck dried. The wet solid was further dried in vacuum oven at 25-35° C. for 1-2 hrs and at 50-60° C. for 8-12 hrs to get 14.2 gms of trigonelline.

HPLC Purity: 99.7%; ROI: 0.23% w/w.

It will be understood that various modifications may be made to the embodiments disclosed herein. Therefore the above description should not be constructed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A process for the preparation of trigonelline of formula I or a pharmaceutically acceptable salts thereof, formula I

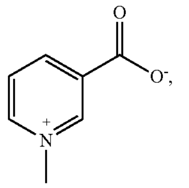

comprising:

a) reacting nicotinic acid of formula II with dimethyl sulfate in a suitable organic solvent to obtain a compound of formula III, wherein the suitable organic solvent is an alcohol, a ketone, an ether, a nitrile, an amide, a halogenated solvent, a cyclic hydrocarbon solvent, an aromatic hydrocarbon solvent, or a mixture thereof, formula II

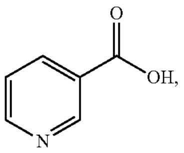

formula III

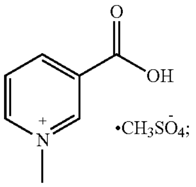

and b) converting the compound of formula III into the trigonelline of formula I or the pharmaceutically acceptable salts thereof.

2. The process as claimed in claim 1, wherein the suitable organic solvent is selected from the group consisting of methanol, isopropanol, ethyl acetate, methyl isobutyl ketone, acetone, acetonitrile, and mixtures thereof.

3. The process as claimed in claim 2, wherein the suitable organic solvent is acetone.

4. The process as claimed in claim 1, wherein the amount of dimethyl sulfate is about 0.8 to 1.2 moles per mole of the nicotinic acid of formula II.

5. The process as claimed in claim 1, wherein the step a) reaction is carried out at 50° C. to about 100° C.

6. The process as claimed in claim 1, wherein the step b) further comprises:

i) reacting the compound of formula III with an acid to obtain a compound of formula IV, formula IV

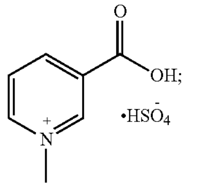

and ii) neutralizing the compound of formula IV with a base to obtain the trigonelline of formula I or the pharmaceutically acceptable salts thereof.

7. The process as claimed in claim 6, wherein the suitable acid is selected from group consisting of hydrochloric acid, hydrobromic acid, hydrofluoric acid, hydroiodic acid, sulfuric acid, phosphoric acid, nitric acid, perchloric acid, and boric acid.

8. The process as claimed in claim 7, wherein the suitable acid is one of sulfuric acid or hydrochloric acid.

9. The process as claimed in claim 6, wherein the base is selected from one or more of the group consisting of sodium hydroxide, sodium methoxide, sodium carbonate, potassium carbonate, sodium bicarbonate, potassium bicarbonate, and mixtures thereof.

10. The process as claimed in claim 9, wherein the base is sodium hydroxide.

11. The process as claimed in claim 6, wherein the step i) is carried out at a temperature of about 40° C. to about reflux temperature.

12. A process for purification of trigonelline of formula I or a pharmaceutically acceptable salts thereof, formula I

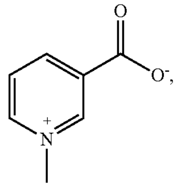

comprising:

a) dissolving or suspending trigonelline or a pharmaceutically acceptable salts thereof in a suitable solvent at about 40° C. to reflux temperature, wherein the suitable solvent is one or more of isopropanol, butanol, tetrahydrofuran, methyl tertiary butyl ether, diisopropyl ether, diethyl ether, acetonitrile, propionitrile, toluene, xylene, heptane, hexane, cyclohexane, methyl cyclohexane, dichloromethane, dichloroethane, chloroform, acetone, methyl ethyl ketone, methyl isobutyl ketone, ethyl acetate, methyl acetate, isopropyl acetate, or mixtures of any of the foregoing with water;

b) cooling the step a) solution to less than 40° C.; and c) isolating the purified trigonelline of formula I or the pharmaceutically acceptable salts thereof.

13. The process as claimed in claim 12, wherein the suitable solvent is one of isopropanol or a mixture of isopropanol and water.

14. A process for the preparation of trigonelline of formula I, formula I

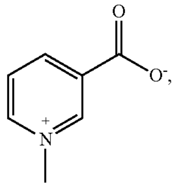

comprising:

a) reacting nicotinic acid of formula II with dimethyl sulfate in a ketone solvent at a temperature to obtain a compound of formula III, formula II

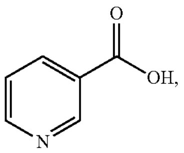

formula III

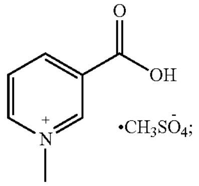

b) reacting the compound of formula III with sulfuric acid to form trigonelline sulfate;

c) isolating the trigonelline sulfate of the compound of formula IV, formula IV

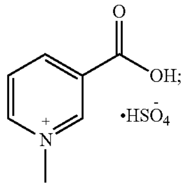

d) neutralizing the compound of formula IV with a base to obtain the trigonelline of formula I;

e) purifying the trigonelline obtained in step d) with a suitable solvent; and f) isolating the purified trigonelline;

wherein the ketone solvent is acetone or methyl isobutyl ketone wherein the base is sodium hydroxide, and wherein the suitable solvent is one of isopropanol or a mixture of isopropanol and water.

15. The process as claimed in claim 14, wherein the purified trigonelline of formula I or a pharmaceutically acceptable salts thereof contains less than 0.1% as measured by HPLC of nicotinic acid of formula II.

16. The process as claimed in claim 14, wherein the purified trigonelline of formula I or a pharmaceutically acceptable salts thereof is characterized by a residue on ignition less than about 0.3 percent by weight.

17. The process as claimed in claim 1, further comprising:

c) combining the trigonelline of formula I or the pharmaceutically acceptable salts thereof with at least one pharmaceutically acceptable excipient to make a pharmaceutical composition.

18. Trigonelline of formula I, a pharmaceutically acceptable salt thereof, or a pharmaceutical composition comprising the trigonelline of formula I or the pharmaceutically acceptable salt thereof with at least one pharmaceutically acceptable excipient, formula I

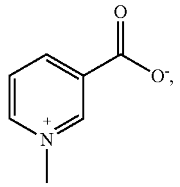

wherein the trigonelline of formula I and the pharmaceutically acceptable salt thereof are characterized by a residue on ignition less than about 0.3 percent by weight and by less than 0.1% as measured by HPLC of nicotinic acid.

* * * * *